United States Patent [19]

Celmer et al.

[11] 4,150,152

[45] Apr. 17, 1979

[54] POLYCYCLIC ETHER ANTIBIOTIC PRODUCED BY A STRAIN OF STREPTOMYCES HYGROSCOPICUS

[75] Inventors: Walter D. Celmer, New London; Walter P. Cullen, East Lyme; Charles E. Moppett, Pawcatuck; John R. Oscarson, Groton; Liang H. Huang, East Lyme, all of Conn.; Riichiro Shibakawa, Handa; Junsuke Tone, Chita, both of Japan

[73] Assignee: Pfizer Inc., New York, N.Y.

[21] Appl. No.: 845,491

[22] Filed: Oct. 26, 1977

[51] Int. Cl.² ............................................ A61K 35/00
[52] U.S. Cl. ................................. 424/122; 195/80 R
[58] Field of Search ....................... 424/122; 195/80 R

[56] References Cited

U.S. PATENT DOCUMENTS 4,069,316  1/1978  Imada et al. .......................... 424/122

*Primary Examiner*—Jerome D. Goldberg
*Attorney, Agent, or Firm*—Connolly and Hutz

[57] ABSTRACT

A new polycyclic ether antibiotic produced by a strain of *Streptomyces hygroscopicus* under submerged fermentation conditions is useful in controlling coccidiosis in poultry and in improving feed utilization efficiency in ruminants.

5 Claims, 2 Drawing Figures

Infrared Absorption Spectrum of Free Acid of Compound 41,224

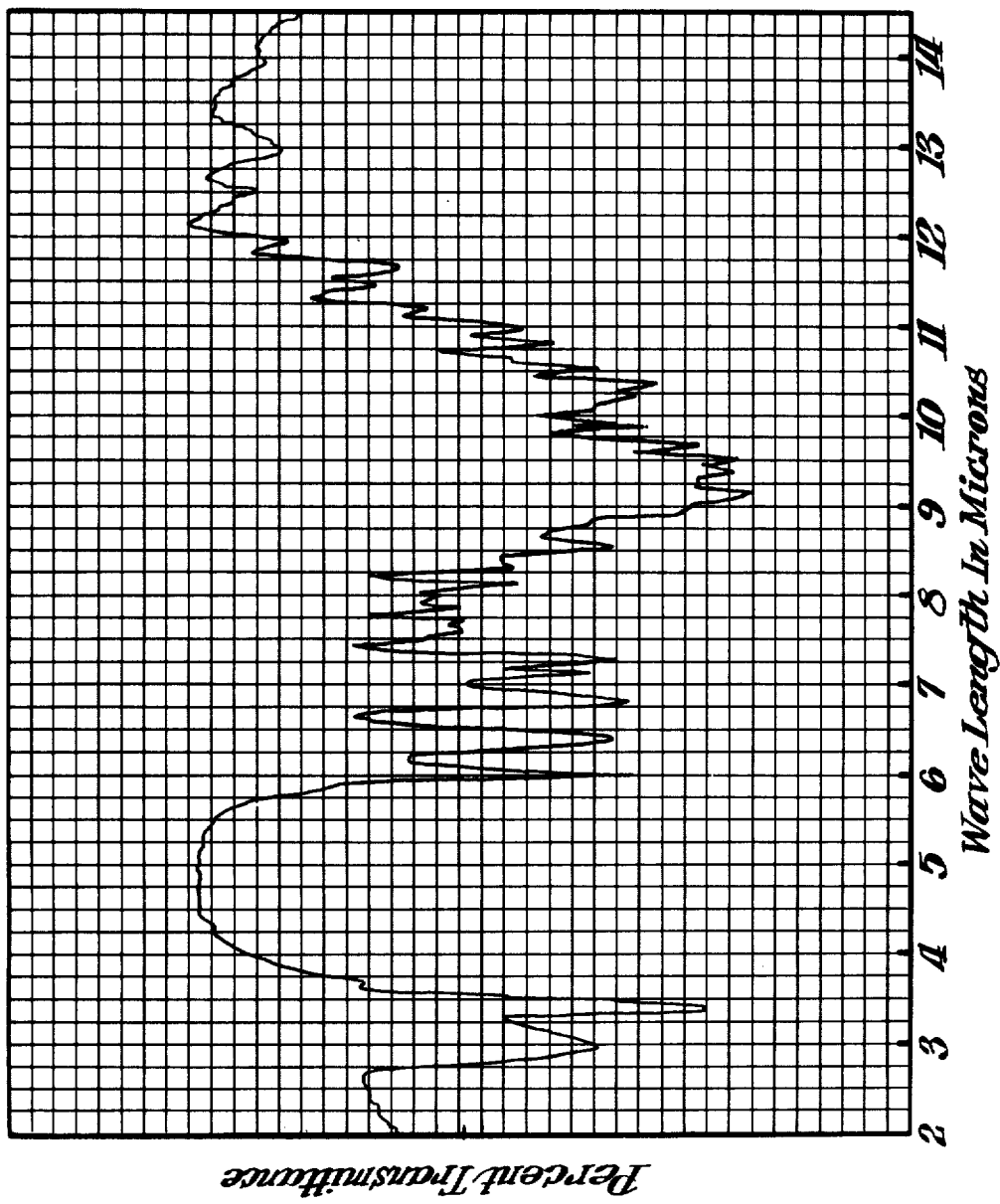

POLYCYCLIC ETHER ANTIBIOTIC PRODUCED BY A STRAIN OF STREPTOMYCES HYGROSCOPICUS

BACKGROUND OF THE INVENTION

This invention is concerned with a new member of the acidic polycyclic ether group of antibiotics, a class of compounds characterized biologically by their effect on cation transport in mitochondria. This family of antibiotics includes monensin (J. Amer. Chem. Soc., 89:5737, 1967); nigericin (Biochem. Biophys. Res. Comm., 33:29, 1968); grisorixin (J. Chem. Soc. Chem. Commun., 1421, 1970); dianemycin (J. Antibiotics, 22:161, 1969); salinomycin (J. Antibiotics, 27:814, 1974); X-537A (J. Chem. Soc. Chem. Commun., 967, 1972); X-206 (J. Chem. Soc. Chem. Commun., 927, 1971); and A204A (J. Amer. Chem. Soc., 95:3399 1973).

The polycyclic ether antibiotics listed above are active against Gram-positive bacteria, fungi and protozoa. These antibiotics exhibit potent anticoccidial activity.

The control of coccidiosis continues to be a serious problem to the poultry industry. There are six species of coccidia which produce easily discernible morbidity in susceptible chickens. *Eimeria tenella, E. necatrix, E. brunetti, E. acervulina, E. maxima* and *E. mivati* produce damage either directly through destruction of epithelial cells of the digestive tract or indirectly through production of toxins. Three other species of protozoa belonging to the same genus are considered to be relatively innocuous. however, *E. mitis, E. hagani* and *E. praecox* are capable of reducing weight gain, lowering feed efficiency and adversely affecting egg production.

The polycyclic ether antibiotics possess a high degree of effectiveness against all species of Eimeria.

SUMMARY OF THE INVENTION

This invention is concerned with a new polycyclic ether antibiotic produced by a strain of *Streptomyces hygroscopicus* under submerged aerobic conditions in aqueous nutrient media. Antibiotic Compound 47,224 and its cationic salts are active against a variety of microorganisms, effective in controlling coccidiosis in poultry and act to improve feed utilization efficiency in ruminants.

DETAILED DESCRIPTION OF THE INVENTION

Figure 1:
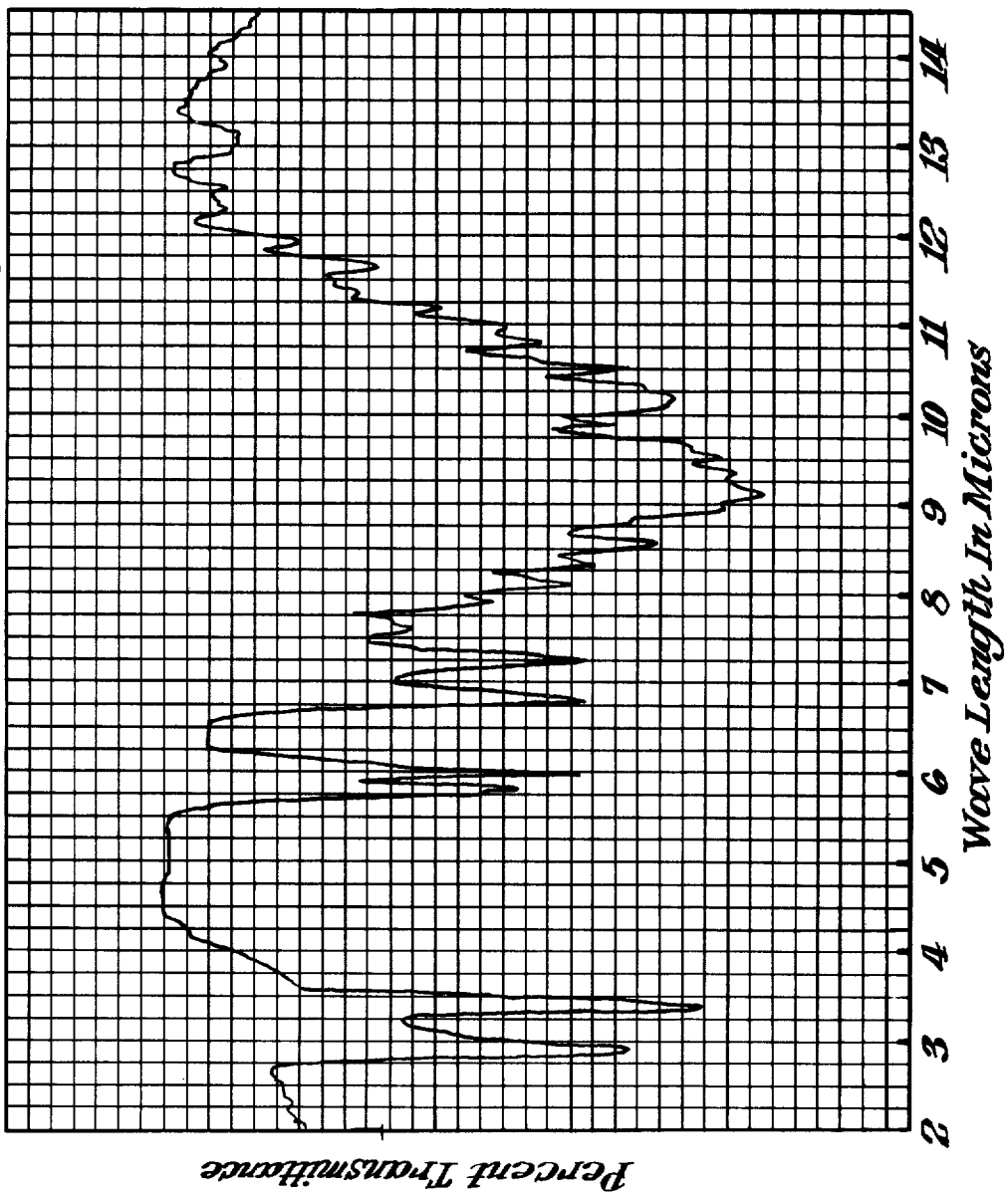

The antibiotic producing microorganism of the present invention, isolated from a soil sample in North Dakota, U.S.A., was identified as a strain of *Streptomyces hygroscopicus* (Jensen) Waksman and Henrici on the basis of the color of spore mass, morphology of spore chains and morphology of the spore surface.

Identification media used for the characterization of the culture and reference for their composition are as follows:

1. Tryptone Yeast Extract Broth - (ISP #1 medium, Difco).
2. Yeast Extract-Malt Extract Agar - (ISP #2 medium, Difco).
3. Oatmeal Agar - (ISP #3 medium, Difco).
4. Inorganic Salts-Starch Agar - (ISP #4 medium, Difco).
5. Glycerol-Asparagine Agar - (ISP #5 medium, Difco).
6. Peptone-Yeast Extract Iron Agar - (ISP #6 medium, Difco).
7. Tyrosine Agar - (ISP #7 medium, Difco).
8. Czapek-Sucrose Agar - S. A. Waksman, The Actinomycetes, Vol. 2, medium no. 1, p. 328, 1961.
9. Glucose Asparagine Agar - Ibid, medium no. 2, p. 328.
10. Glucose-Yeast Extract Agar - Ibid, Medium no. 29, p. 331.
11. Emerson's Agar - Ibid, medium no. 28, p. 331.
12. Nutrient Agar - Ibid, medium no. 14, p. 330.
13. Gordon and Smith' tyrosine Agar - R. E. Gordon and M. M. Smith. Jr. Bact. 69:147-150, 1955.
14. Casein Agar - Ibid.
15. Calcium Malate Agar - S. A. Waksman, Bact. Rev. 21:1-29, 1957.
16. Gelatin - R. E. Gordon and J. M. Mihm, Jr. Bact. 73:15-27, 1957.
17. Starch - Ibid.
18. Organic Nitrate Broth - Ibid.
19. Dextrose Nitrate Broth - S. A. Waksman, The Actinomycetes, Vol. 2, medium no. 1, p. 328, 1961, with 3 g dextrose substituted for 30 g sucrose and agar omitted
20. Potato Carrot Agar - M. P. Lechevalier, Jr. Lab. and Clinical Med. 71:934-944, 1968 but use only 30 g potatoes, 2.5 g carrots and 20 g agar.
21. 2% Tap Water Agar.
22. Skim Milk - Difco.
23. Cellulose utilization - (a) H. L. Jensen, Proc. Linn. Soc. N.S.W. 55:231-248, 1930. (b) M. Levine and H. W. Schoenlein, A Compilation of Culture Media, medium no. 2511, 1930.
24. Carbohydrates - ISP #9 medium, Difco.
25. Temperature Range - ATCC medium 172 in ATCC Culture Collection Catalogue, 12th ed. p. 329, 1976.

The culture was described as follows on the various media:

Yeast Extract-Malt Extract Agar - Growth good, white, off-white to cream (near gray series 1 ba), raised, wrinkled; reverse yellowish brown; with pale yellowish brown soluble pigment.

Oatmeal Agar - Growth moderate to good; lavender (5 ig to 5 li), occurring as small isolated dots, with lavender aerial mycelium; reverse grayish; soluble pigment very pale greenish.

Inorganic Salts-Starch Agar - Growth moderate, white to pale grayish (2 ec) but yellowish (near 1 ea) near the edge, thin, smooth to slightly roughened, with white to pale grayish aerial mycelium; reverse pale yellowish; with pale yellowish soluble pigment.

Glycerol-Asparagine Agar - Growth poor, off-white, thin, smooth, with scant white aerial mycelium; reverse colorless; no soluble pigment.

Gordon and Smith' Tyrosine Agar - Growth moderate, pale grayish (near 2 ec), slightly raised and roughened, with scant pale grayish aerial mycelium; reverse yellowish brown to brown; with brown (4 pi) soluble pigment.

Czapek-Sucrose Agar - Growth moderate, pale grayish (between 2 ca and 2 ec), thin, smooth, with scant bloomy aerial mycelium; reverse colorless; with very pale pinkish soluble pigment.

Glucose-Asparagine Agar - Growth good, grayish (3 ge, 3 ig to near gray series 2 fe), raised, wrinkled, with aerial mycelium, producing yellowish exudate near the edge of steak; reverse colorless to brown; with yellowish (1½ ga) soluble pigment.

Calcium Malate Agar - Growth poor, colorless to white, thin, smooth, occurring as isolated small dots; reverse colorless; no soluble pigment.

Casein Agar - Growth moderate to good, colorless to pale cream, thin, wrinkled, no aerial mycelium; reverse same as surface; with pale pinkish soluble pigment.

Glucose-Yeast Extract Agar - Growth good; white to cream, raised, wrinkled, with white aerial mycelium; reverse cream to pale yellowish brown; with yellowish brown (3 nc) soluble pigment.

Emerson's Agar - Growth moderate to good, off-white, highly raised, wrinkled, with white bloomy aerial mycelium; reverse cream; with yellowish brown (3 pc) soluble pigment.

Nutrient Agar - Growth moderate, off-white, slightly raised and roughened, with scant aerial mycelium; reverse colorless; no soluble pigment.

Gelatin Agar - Growth good, off-white, slightly raised and roughened, with aerial mycelium; reverse pale yellowish brown; no soluble pigment.

Starch Agar - Growth good, off-white, slightly raised and wrinkled, with white aerial mycelium; reverse yellowish brown; no soluble pigment.

Potato Carrot Agar - Growth moderate, lavender (4 ig), occurring as isolated, slightly raised spots, with aerial mycelium; reverse same as surface; no soluble pigment.

Tap Water Agar - Growth poor to moderate, grayish lavender (3 ge to 3 ig), thin, occurring as isolated spots, with aerial mycelium; reverse same as surfaces; no soluble pigment.

Biochemical Properties - Melanin not produced; hydrogen sulfide not produced; gelatin liquefied; starch hydrolyzed; nitrate not reduced to nitrite on both media; growth on Jensen's cellulose, scant growth on Levine and Schoenlein's cellulose, no decomposition on both cellulose media; clearing and peptonization on milk; casein digestion positive; no digestion of calcium malate. Carbohydrate utilization: glucose, fructose, mannitol, arabinose, raffinose, inositol, rhamnose, sucrose and xylose utilized.

Morphological Properties - Spore mass in gray color series; sporophores monopodial, or rarely verticillate, unbranched, or rarely once-branched; spore chains in spirals which were narrow, slightly open, consisted of 4 to 8 turns and tended to develop in clusters which often absorbed moisture; 10 to 50 spores per spore chain; spores warty, or rarely smooth, oval, short rod-shaped to rod shaped, 1-1.4 μm or 1.4-1.8-×1-1.2 μm.

| Temperature Relations | | | |
|---|---|---|---|
| 21° C. | 28° C. | 37° | 45° |
| good growth | good to excellent growth | good growth | poor growth |

Although the culture differs from the neotype described in Int. J. Syst. Bact. 22:265-394, 1972, in its ability to utilize sucrose and raffinose, Tresner and Backus, Applied Microbiology 4:243-250, 1956, found that strains of *Streptomyces hygroscopicus differ in their utilization of carbon source and hence carbohydrate utilization is a variable feature to be used in the taxonomy of this group of organisms.*

The strain of *Streptomyces hygroscopicus* has been deposited at the American Type Culture Collection with the accession number ATCC 31337.

The permanency of the deposit of this culture at The American Type Culture Collection in Rockville, Maryland and ready accessibility thereto by the public are afforded throughout the effective life of the patent. Access to the culture is available during pendency of the application under Rule 14 and 35 USC 112. All restrictions on the availability to the public of the cultures deposited will be irrevocably removed upon granting of the patent.

Cultivation of *Streptomyces hygroscopicus* preferably takes place in aqueous nutrient media at a temperature of 24° to 36° C., and under submerged aerobic conditions with agitation. Nutrient media which are useful for such purposes include a source of assimilable carbon such as sugars, starches and glycerol; a source of organic nitrogen such as casein, enzymatic digest of casein, soybean meal and fish meal. A source of growth substances such as grain solubles and yeast extract as well as salts such as sodium chloride and calcium carbonate and trace elements such as iron, magnesium, zinc, cobalt and manganese may also be utilized with advantageous results. If excessive foaming is encountered during fermentation, antifoam agents such as vegetable oils or silicones may be added to the fermentation medium. Aeration of the medium in tanks for submerged growth is preferably maintained at the rate of about ½ to 2 volumes of air per volume of broth per minute. Agitation may be maintained by means of agitators generally familiar to those in the fermentation industry. Aseptic conditions must, of course, be maintained through the transfer of the organism and throughout its growth.

Inoculum for the preparation of the antibiotic may be obtained by employing growth from a slant of the culture. The growth may be used to inoculate either shake flasks or inoculum tanks or the inoculum tanks may be seeded from the shake flasks. Growth in shaken flasks will generally have reached its maximum in 3 to 5 days whereas inoculum in submerged inoculum tanks will usually be at the most favorable period in 3 to 4 days. Substantial antibiotic activity is obtained in the final fermentor stage in approximately 2 to 5 days. The antibiotic levels range from 25 to 250 mg per liter.

The process of antibiotic production is conveniently followed during fermentation by biological assay of the broth employing a sensitive strain of *Staphylococcus aureus* or *Bacillus subtilis*. Standard plate assay technique is employed in which the zone of inhibition is used as a measure of antibiotic potency.

Thin-layer chromatography employing silica gel is a useful tool for analyzing the antibiotics produced in fermentation media and the composition of crude and purified materials extracted from the fermentation broths. The Analtech silica gel GF chromatograms are developed with ethyl acetate. Antibiotic Compound 47,224 may be visualized by exposure to 254 nm light or by spraying with 3% vanillin in ethanolic sulphuric acid (97:3, v/v) where it shows up as a green spot on a white background after warming on a steam bath or a hot plate. Bio-overlay with agar seeded with a sensitive strain of *Staphylococcus aureus* or *Bacillus subtilis* is a further procedure for detection of the antibiotic.

Antiobiotic Compound 47,224 may be separated and recovered by extracting the whole, unfiltered fermentation broth with an organic solvent such as chloroform, ethyl acetate, methylisobutyl ketone or butanol at a pH range of 4.0 to 10.0. A major portion of the antibiotic activity is contained in the mycelium and may be extracted therefrom by slurring the separated mycelium with a watersoluble solvent such as methanol. The solvent is concentrated to a thin syrup.

A method of separation and recovery of antibiotic Compound 47,224 is as follows: Whole fermentation broth without pH adjustment is extracted with about ⅓ volume of methylisobutyl ketone. The solvent extract is concentrated in vacuo to an oily concentrate. The concentrate is dissolved in heptane and poured onto a bed of column grade silica gel contained in a sintered glass funnel. The silica gel is washed successively with heptane, toluene, chloroform, ethyl acetate and methanol. The antibiotic resides primarily in the ethyl acetate fraction with lesser amounts in the chloroform and methanol fractions. The active fractions are further purified by column chromatography on silica gel developed with chloroform. Active fractions are combined and evaporated to give a viscous oil which is further chromatographed on a silica gel column and eluted with chloroform:acetone (9:1, v/v) to provide a viscous pale yellow oil. This material is further purified by chromatography on silica gel developed with chloroform:acetone (9:1, v/v). Active fractions are combined, stirred with activated charcoal in acetone, filtered and evaporated. The derived solids are converted to the sodium salt by first dissolving in chloroform and then washing with pH 4 aqueous solution and then with water adjusted to pH 10. The chloroform layer is dried over anhydrous sodium sulphate and then evaporated to a white solid.

Antibiotic Compound 47,224 exhibits inhibitory action against the growth of a number of Gram-positive microorganisms. This compound and its cationic salts exhibit excellent activity against coccidial infections in poultry. When incorporated into the diet of chickens at levels of 5 to 100 ppm, these compounds are effective in controlling infections due to *Eimeria tenella, Eimeria acervulina, Eimeria maxima, Eimeria brunetti* and *Eimeria necatrix*.

Efficacy data for Compound 47,224 and its cationic salts against coccidial infections in chickens were obtained as follows: Groups of 3-5 ten-day old SPF white leghorn cockerel chicks were fed a mash diet containing antibiotic Compound 47,224 or its sodium and/or potassium salt uniformly dispersed therein. After being on this ration for 24 hours, each chick was inoculated per os with oocysts of the particular species of Eimeria being tested. Other groups of 3-5 ten-day-old chicks were fed a similar mash diet free from antibiotic Compound 47,224 or its salts. They were also infected after 24 hours and served as infected controls. Still other groups of chicks were fed the mash diet free of antibiotic Compound 47,224 and were not infected with coccidia. These served as normal controls. The results of treatment were evaluated after five days in the case of *E. acervulina* and six days for all other challenges.

| Speceis Infection | Dose (ppm) | Average Degree[1] of Infection | Ratio[1] | Weight Gain (%) |
|---|---|---|---|---|
| Eimeria tenella | 30 | 0.0 | 0.0 | 46 |
| | 15 | 0.3 | 0.1 | 75 |
| | 7.5 | 1.0 | 0.3 | 58 |
| | 3.8 | 2.3 | 0.77 | 46 |
| | 1.9 | 2.7 | 0.9 | 60 |
| Eimeria acervulina | 30 | 0.4 | 0.2 | 0 |
| | 15 | 0.8 | 0.4 | 38 |
| | 7.5 | 1.2 | 0.6 | 62 |
| | 3.8 | 2.0 | 1.0 | 26 |
| | 1.9 | 2.0 | 1.0 | 0 |
| Eimeria necatrix | 30 | 0.0 | 0.0 | 7 |
| | 15 | 0.0 | 0.0 | 59 |
| | 7.5 | 0.8 | 0.4 | 75 |
| | 3.8 | 1.0 | 0.5 | 97 |
| | 1.9 | 1.6 | 0.8 | 53 |
| Eimeria maxima | 30 | 0.8 | 0.67 | 22 |
| | 15 | 0.6 | 0.5 | 36 |
| | 7.5 | 0.6 | 0.5 | 59 |
| | 3.8 | 1.3 | 1.08 | 71 |
| | 1.9 | 1.2 | 1.0 | 47 |
| Emieria brunetti | 30 | 0.6 | 0.33 | 17 |
| | 15 | 0.6 | 0.33 | 44 |
| | 7.5 | 0.6 | 0.33 | 83 |
| | 3.8 | 1.4 | 0.78 | 44 |
| | 1.9 | 1.4 | 0.78 | 39 |

The value of animal feeds generally has been determined directly by feeding the animal. Great Britain Pat. No. 1,197,826 details an in vitro rumen technique whereby the changes occurring in feeds brought about by microorganisms are measured more readily and with great accuracy in the evaluation of animal feeds. This technique involves the use of an apparatus in which the digestive processes of the aminals are conducted and studied in vitro. The animal feeds, rumen inoculum and various growth promotants are introduced into and withdrawn from a laboratory unit under carefully controlled conditions and the changes taking place are studied critically and progressively during the consumption of the feed by the microorganisms. An increase in the propionic acid content in the rumen fluid indicates that a desirable response in overall ruminant performance has been brought about by the growth promotant in the feed composition. The change in propionic acid content is expressed as percent of the propionic acid content found in the control rumen fluid. Long term in vivo feeding studies are used to show a reliable correlation between propionic acid increase in the rumen fluid and improved animal performance.

Rumen fluid is collected from a fistulated cow which is fed on a commercial fattening ratio plus hay. The rumen fluid is immediately filtered through cheese cloth, and 10 ml added to a 50 ml conical flask containing 400 mg. of standard substrate (68% corn starch + 17% cellulose + 15% extracted soybean meal), 10 ml of a pH 6.8 buffer and the test compound. The flasks are gassed with oxygen-free nitrogen for about two minutes, and incubated in a shaking water bath at 39° C. for about 16 hours. All tests are conducted in triplicate.

After incubation, 5 ml of the sample are mixed with 1 ml of 25% metaphosphoric acid. After 10 minutes, 0.25 ml of formic acid is added and the mixture centrifuged at 1,500 r.p.m. for 10 minutes. Samples are then analyzed by gas-liquid chromatography by the method of D. W. Kellog, J. Dairy Science 52, 1690 (1969). Peak heights for acetic, propionic and butyric acids are determined for samples from untreated and treated incubation flasks.

When tested by this in vitro method, 20 ppm of the sodium salt of Compound 47,224 gave rise to a 35% increase in the production of propionic acid over that produced in the control solution without added Compound 47,224. Similar results may be obtained with other pharmaceutically acceptable salts or the free acid of Compound 47,224.

Based on these data, it can be projected that improvement of feed utilization by ruminants such as cattle and sheep and monogastric animals such as horses, pigs and rabbits will be comparable with that obtained by commercially available Monensin, a polycyclic ether antibiotic. Antibiotic Compound 47,224 may be incorporated in feed compositions as the free acid, sodium salt, potassium salt or mixtures thereof. Crude Compound 47,224 or dried fermentation broth containing the antibiotic may be incorporated in feed compositions at the desired potency concentrations.

EXAMPLE 1

A sterile aqueous medium having the following composition was prepared:

| Ingredient | Grams/liter |
| --- | --- |
| Glucose | 10 |
| Starch | 20 |
| Yeast extract | 5 |
| Enzymatic digest of casein | 5 |
| Dipotassium hydrogen phosphate | 0.5 |
| Meat meal | 5 |
| Cobalt chloride | 0.002 |
| Calcium carbonate | 4 |
| pH 7.1–7.2 | |

Cells from a slant of *Streptomyces hygroscopicus* ATCC 31337 were transferred to a series of 300 ml flasks each containing 50 ml of this sterile medium and shaken on a rotary shaker at 28°–30° C. for 3–4 days. An aliquot of the grown culture, sufficient to provide 2–4% v/v inoculum, was transferred to 4-liter fermentors each containing two liters of the following sterile medium:

| Ingredient | Grams/liter |
| --- | --- |
| Glucose | 20 |
| Soy flour | 20 |
| Ferric sulfate | 0.3 |
| Manganese chloride | 0.3 |
| Cobalt chloride | 0.002 |
| pH 6.9–7.1 | |

The fermentation was conducted at 30° C. with stirring at 1700 revolutions per minute and aeration at one volume of air per volume of broth per minute until substantial activity was obtained (2–5 days). The whole broth, without pH adjustment, was twice extracted with ⅛ to ½ volume of methylisobutyl ketone. The separated solvent extracts were combined and concentrated under vacuum to a thin syrup.

EXAMPLE 2

The inoculum medium of Example 1 was distributed in 700 ml amounts in a number of shake flasks and inoculated with cells of *Streptomyces hygroscopicus* ATCC 31337. After incubation at 28° C. on a rotary shaker for 3 to 5 days, a 4% v/v inoculum was introduced into a 50 gallon fermentor containing the production fermentation medium of Example 1. The fermentation was conducted at 30° C. until substantial antibiotic activity was obtained (approximately 5 days).

Approximately 28 gallons of the final whole fermentation broth, without pH adjustment, was extracted with about 15 gallons of methylisobutyl ketone. The solvent extract was concentrated under vacuum to provide 125 grams of an oily concentrate.

The oily concentrate was dissolved in heptane and poured onto a bed of 1.1 kg of column grade silica gel 60 (E. Merck, Darmstadt, Germany) contained in a large sintered glass funnel. The silica gel was washed with 5 liters each of heptane, toluene, chloroform, ethyl acetate and methanol. These eluates were examined by thin-layer chromatography. Antibiotic Compound 47,224 was found to reside primarily in the ethyl acetate fraction (37 grams) with lesser amounts being found in the chloroform (4.1 grams) and methanol (27 grams) fractions. The other fractions were discarded.

The antibiotic-containing fractions were evaporated in vacuo, dissolved in chloroform and chromatographed on a silica gel 60 column developed with chloroform. The column fractions containing Compound 47,224 were combined and evaporated to give 16.0 grams of a viscous oil which was further chromatographed on a silica gel 60 column and eluted with chloroform:acetate (9:1, v/v) to provide 8.5 grams of a viscous pale yellow oil (approximately 50% Compound 47,224 by UV assay).

The material was further purified by chromatography on silica gel 60 and developed with chloroform:acetatone (9:1, v/v). Fraction cuts containing Compound 47,224 were stirred with activated charcoal (Darco G60), 0.5 grams per gram of antibiotic, filtered and evaporated. The derived solids were converted to the sodium salt by first dissolving in chloroform and then washing with pH 4 aqueous solution (water adjusted to pH 4 with 85% phosphoric acid) and then with pH 10 aqueous solution (water adjusted to pH 10.0 with 1.0 N NaOH). The chloroform layer was dried over sodium sulphate and evaporated, whereupon Compound 47,224 solidified as a white foam. Drying in vacuo at room temperature for 3 hours gave a final weight of 4.5 grams. This material could not be induced to crystallize.

An analytical sample of the sodium salt of Compound 47,224 was obtained by preparative thin-layer chromatography on Analtech silica gel GF developed with ethyl acetate. The desired Compound 47,224 was detected by exposure to 254 nm light, eluted from the silica gel with acetone and taken to the sodium salt as described above. It could not be induced to crystallize.

The sodium salt of Compound 47,224 is soluble in chloroform, ethyl acetate and methylisobutyl ketone; it is insoluble in water. In a melting point determination, the compound shrinks at 60° C. and melts at 142°–157° C. The average composition by weight is 60.82% carbon and 8.55% hydrogen; an optical rotation of $[\alpha]_D = +35°$ (c=1.0, methanol); absorption maximum in methanol in the ultraviolet light region of the spectrum at 232 nm, $E_1\ _{cm}{}^{1\%} = 150$; and when pelleted in KBr, distinguishable bands in the infrared region as shown in FIG. 2 at the following wavelengths in microns: 2.95, 3.40, 6.00, 6.40, 6.85, 7.30, 8.10, 8.55, 9.15, 10.50, 10.80, 11.70 and 11.95.

The free acid of Compound 47,224 was derived by washing a chloroform solution of the sodium salt of Compound 47,224 with a pH 4.0 aqueous solution (water adjusted to pH 4.0 with 85% phosphoric acid). The solvent layer was evaporated in vacuo to afford an amorphous mass that could not be induced to crystallize. The compound, m.p. 65° C. (shrink) 68°–80° C., is soluble in methanol, acetone, chloroform, methylisobutyl ketone and ethyl acetate; it is insoluble in water.

The free acid is characterized by an average composition by weight of 62.50% carbon, 8.92% hydrogen and 28.58% oxygen (by difference); absorption maximum in methanol in the ultraviolet light region of the spectrum at 232 nm, $E_{1\ cm}^{1\%} = 150$; an optical rotation of $[\alpha]_D = +43°$ (c = 1.0, methanol); and when pelleted in KBr, distinguishable bands in the infrared region as shown in FIG. 1 at the following wavelengths in microns: 2.90, 3.40, 5.85, 6.00, 6.82, 7.25, 8.10, 8.57, 9.15, 10.50, 10.80, 11.65 and 11.95.

EXAMPLE 3

The method of Example 2 may be repeated employing a fermentation medium of the following composition:

| Ingredient | Grams/liter |
|---|---|
| Glucose | 1 |
| Soy flour | 10 |
| Corn starch | 10 |
| Grain solubles | 5 |
| Ferric sulfate | 0.2 |
| Manganese chloride | 0.2 |
| Cobalt chloride | 0.002 |
| Sodium chloride | 5 |
| Methyl oleate | 2 |
| Calcium carbonate | 1 |
| Soybean oil | 2 |
| pH 6.9–7.1 | |

What is claimed is:

1. The antibiotic Compound 47,224, or the pharmaceutically acceptable cationic salts thereof, said antibiotic when in the form as the free acid is soluble in methanol, acetone, chloroform, methylisobutyl ketone, ethyl acetate and insoluble in water; has a melting point of 65° C. (shrink) 68°–80° C.; an optical rotation of $[\alpha]_D = +43°$ at a concentration of 1% in methanol; an average composition by weight of 62.50% carbon, 8.92% hydrogen and 28.58% oxygen (by difference); ultraviolet light absorption maximum in methanol of 232 nm, $E_{1\ cm}^{1\%} = 150$; and when pelleted in KBr, exhibits characteristic absorption in the infrared at the following wavelengths in microns: 2.90, 3.40, 5.85, 6.00, 6.82, 7.25, 8.10, 8.57, 9.15, 10.50, 10.80, 11.65 and 11.95.

2. The antibiotic Compound 47,224 of claim 1 when in the form as the sodium salt.

3. A process for producing the antibiotic compound 47,224 of claim 1 which comprises cultivating the microorganism *Streptomyces hygroscopicus* ATCC 31337 in aqueous culture media containing an assimilable source of carbon, nitrogen and inorganic salts until substantial antibiotic activity is obtained.

4. A process according to claim 3 wherein said antibiotic is separated from the fermentation medium.

5. A process according to claim 3 wherein the fermentation medium is taken to dryness.

* * * * *